(12) United States Patent
Wall et al.

(10) Patent No.: US 7,713,553 B2
(45) Date of Patent: May 11, 2010

(54) METHOD OF MANUFACTURE OF A LIQUID PESTICIDE CONTAINING COPPER AND A LIQUID PESTICIDE CONTAINING COPPER

(75) Inventors: Wesley James Wall, Edmonton (CA); Calvin Lee Michael Wall, Edmonton (CA); Ryan George Smart, Edmonton (CA)

(73) Assignee: Genics Inc., Acheson (CA)

( * ) Notice: Subject to any disclaimer, the term of this patent is extended or adjusted under 35 U.S.C. 154(b) by 672 days.

(21) Appl. No.: 10/489,809

(22) PCT Filed: Sep. 16, 2002

(86) PCT No.: PCT/CA02/01403

§ 371 (c)(1),
(2), (4) Date: Oct. 12, 2004

(87) PCT Pub. No.: WO03/024230

PCT Pub. Date: Mar. 27, 2003

(65) Prior Publication Data

US 2005/0058723 A1    Mar. 17, 2005

(30) Foreign Application Priority Data

Sep. 17, 2001  (CA) .................................. 2357392

(51) Int. Cl.
*A01N 59/20* (2006.01)
*A01N 59/14* (2006.01)

(52) U.S. Cl. .................... 424/630; 424/489; 424/635

(58) Field of Classification Search ................ 424/630, 424/632–635, 637, 660, 489; 514/951
See application file for complete search history.

(56) References Cited

U.S. PATENT DOCUMENTS

| | | | |
|---|---|---|---|
| 2,194,827 A | 3/1940 | Gordon | |
| 2,573,253 A | 10/1951 | Farber | |
| 3,007,844 A | 11/1961 | Shulz et al. | |
| 4,292,382 A | 9/1981 | Lecerf et al. | |
| 4,759,872 A | 7/1988 | Marx et al. | |
| 4,761,179 A | 8/1988 | Goettsche et al. | |
| 5,194,323 A | 3/1993 | Savoy | |
| 5,221,758 A | 6/1993 | Maynard | |
| 5,270,108 A | 12/1993 | Savoy | |
| 5,458,906 A | 10/1995 | Liang | |
| 5,478,598 A * | 12/1995 | Shiozawa ................... | 427/297 |
| 5,527,384 A | 6/1996 | Williams et al. | |
| 5,612,094 A | 3/1997 | Schubert et al. | |
| 5,635,217 A | 6/1997 | Goettsche et al. | |
| 5,853,766 A | 12/1998 | Goettsche et al. | |
| 5,906,828 A | 5/1999 | Cima | |
| 5,916,356 A | 6/1999 | Williams et al. | |
| 6,001,279 A | 12/1999 | Payzant et al. | |
| 6,042,848 A | 3/2000 | Lawyer et al. | |
| 6,045,818 A | 4/2000 | Cima | |
| 6,080,796 A | 6/2000 | Liebert et al. | |
| 6,093,422 A | 7/2000 | Denkewicz | |
| RE36,798 E | 8/2000 | Williams et al. | |
| 6,143,318 A | 11/2000 | Gilchrist et al. | |
| RE37,133 E | 4/2001 | Maynard | |
| 6,291,549 B1 | 9/2001 | Mechtel et al. | |
| 6,306,202 B1 | 10/2001 | West | |
| 6,365,066 B1 | 4/2002 | Podszun et al. | |
| 7,160,606 B2 * | 1/2007 | Wall et al. ................ | 428/292.4 |

FOREIGN PATENT DOCUMENTS

| | | |
|---|---|---|
| CA | 2 178 873 | 12/1997 |
| DE | 4 036 778 A1 | 5/1992 |
| EP | 0 450 568 A2 | 10/1991 |
| SU | 190547 A | 12/1966 |
| WO | WO 96 23636 | 8/1996 |

OTHER PUBLICATIONS

CABA abstract 2001:54602 (Jun. 2001).*
Singh, A. K. et al., "Evaluation of fungicides for the management of Taphrina leaf blotch of turmeric (*Curcuma longa* L.)," Journal of Spices and Aromatic Crops, vol. 9(1), pp. 69-71 (2000).*
Derwent Abstract 1986-177005; abstracting DE 3447027 (1986).*
Richardson, H. Wayne. Copper Compounds, Encylopedia of Chemical Technology, Fourth Edition, vol. 7, John Wiley & Sons, 1993.
Sheard, Len. "Evaluation of Boracol Rh and Impel Boron Rods:—A Literature Review", Jun. 12, 1990.
Findlay, W. P. K. "Boron Compounds for the PreseRrvation of Timber Against Fungi and Insects", German Wood Research association 6th Wood Protection Congress, Jul. 1959.

(Continued)

*Primary Examiner*—John Pak
(74) *Attorney, Agent, or Firm*—Christensen O'Connor Johnson Kindness PLLC

(57) ABSTRACT

A method of manufacture of a liquid pesticide containing copper. A first step involves forming of a solidified water soluble copper-borate complex. A second step involves dissolving the solidified water soluble copper-borate complex in water, until the water contains a concentration of at least 0.02% by weight of copper.

3 Claims, 1 Drawing Sheet

OTHER PUBLICATIONS

Freel, Dan, Chris Maples, Bruce Niederer, William Reynolds, and James Watson. "The Effect of Ethylene Glycol and Sodium Borate Solutions on the Adhesion of Epoxy to White Oak and White Pine Samples", Internet on-line, Available from http://www.maritime.org/conf-sched.htm, Dec. 19, 1997.

Rand, Thomas Schools: G. Ph. D. "An assessment of Mold ContaminationProblems in Atlantic Canada Schools: Mold Burdens, Amplifying Sites and Benefits of Proactive School Inspection Policies". Public and Occupational Health Issues, Department of Biology, Saint Mary's University, Halifax, Nova Scotia, as early as 2001.

Williams, Lonnie H. and Terry L. Amburgey. "Integrated Protection against lyctid beetle infestations IV Resistance of boron-treated wood to insect and fungal attack", Forest Products Journal 37(2):10-17, Feb. 1987.

* cited by examiner

METHOD OF MANUFACTURE OF A LIQUID PESTICIDE CONTAINING COPPER AND A LIQUID PESTICIDE CONTAINING COPPER

FIELD OF THE INVENTION

The present invention relates to a method of manufacture of a liquid pesticide containing copper and a liquid pesticide containing copper.

BACKGROUND OF THE INVENTION

Copper has know properties as a fungicide. Unfortunately, copper hydroxide is almost insoluble in water and, therefore, must be dissolved in mineral acids and ammonia forming salt solutions or copper amine complexes.

SUMMARY OF THE INVENTION

What is required is more user friendly and environmentally friendly liquid pesticide containing copper.

According to one aspect of the present invention there is provided a method of manufacture of a liquid pesticide containing copper. A first step involves forming of a solidified water soluble copper-borate complex. A second step involves dissolving the solidified water soluble copper-borate complex in water, until the water contains a concentration of at least 0.02% by weight of copper.

According to another aspect of the present invention there is provided a liquid pesticide containing copper which consists of a copper-borate complex dissolved in water with a concentration of at least 0.02% by weight of copper.

U.S. Pat. No. 6,001,279 (Payzant et al) discloses a method of making a solidified water soluble wood preservative which contains both copper and boron. During laboratory tests a first surprising discovery has been made. It was discovered that a chemical change had occurred to the copper and boron forming a copper-borate complex. During solubility tests a second surprising discovery was made. It was discovered that copper remained in solution when the solidified copper-borate complex was dissolved in water.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
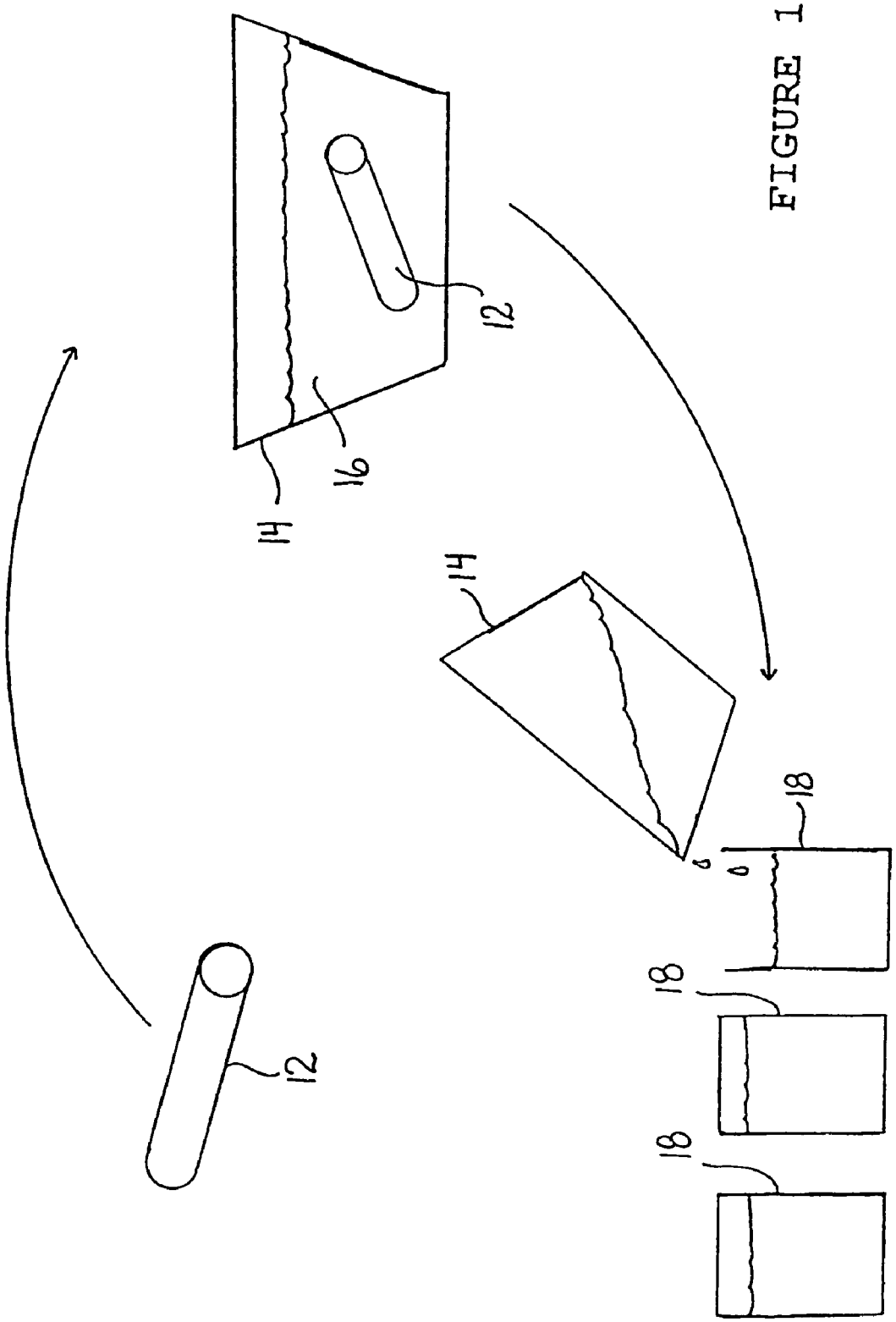
FIG. 1 is a flow diagram illustrating the steps of in the manufacture of a liquid pesticide containing copper in accordance with the teachings of the present invention.

The preferred method of manufacture of a liquid pesticide containing copper will now be described with reference to FIG. 1.

A first step involves forming of a solidified water soluble copper-borate complex 12. The manner of forming of the soluble copper-borate complex is outlined in U.S. Pat. No. 6,001,279. A second step involves dissolving the solidified water soluble copper-borate complex 12 in a container 14 containing water 16. It is preferred that the copper-borate complex be crushed into a granular form, as this accelerates the rate at which the solidified water soluble copper-borate complex will dissolve in water. The resulting water containing the dissolved copper-borate complex can then transferred into small containers 18 to be used as a liquid pesticide. The relative proportions of copper and boron in the copper-borate complex can vary as long as the resulting concentration of in copper in the water has sufficient toxicity for intended use as a moldicide, an insecticide or as a fungicide. For use as a moldicide the concentration of copper in water should be at least 0.20% concentration by weight to have sufficient toxicity to be toxic to molds. For use as an insecticide the concentration of copper in water should be at least 0.30% concentration by weight to have sufficient toxicity to be toxic to insects. For use as a fungicide the concentration of copper in water should be at least 0.20% concentration by weight to have sufficient toxicity to be toxic to fungi.

In terms of minimum and maximum ranges, the minimum range in order to have efficacy is 0.20% by weight. When copper is present in less than 0.20% it is simply not potent enough to be effective. The maximum range is 1.00% as the "excess" copper above this range does not remain in solution. The preferred range is 0.35% by weight to 0.50% by weight. The lower percentage of 0.35% percent of this range has been selected as having efficacy as a moldicide, insecticide and fungicide. The higher percentage of 0.50% of this range has been selected for financial reasons. A percentage of 0.60% is no more effective than a percentage of 0.50%, but is more expensive.

Once the teachings of the present invention are understood, it will be possible for persons skilled in the art to manufacture and sell contains of granules of a solidified water soluble copper-borate complex, together with written instructions regarding dissolving specified quantities of the granules of the solidified water soluble copper-borate complex in specified quantities of water to form a liquid pesticide. The precise quantities of granules and the precise quantities of water required, will be dependent upon the potency of the solidified water soluble copper-borate complex.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. A method of manufacture of a liquid pesticide containing copper, comprising the steps of:
   forming a solidified water soluble copper-borate complex;
   reducing the solidified water soluble copper-borate complex to granules; and
   dissolving the granules of the solidified water soluble copper-borate complex in water to form a liquid pesticide having a concentration of at least 0.20% and not more than 1.00% by weight of copper.

2. The method as defined in claim 1, the concentration of copper in water being not less than 0.35% by weight and not more than 0.50% by weight.

3. A liquid pesticide produced in accordance with the method set forth in claim 1.

* * * * *